US009508149B2

(12) United States Patent
Simon et al.

(10) Patent No.: US 9,508,149 B2
(45) Date of Patent: Nov. 29, 2016

(54) VIRTUAL 3D OVERLAY AS REDUCTION AID FOR COMPLEX FRACTURES

(71) Applicant: Stryker Trauma GmbH, Schönkirchen (DE)

(72) Inventors: Bernd Simon, Kiel (DE); Arno Blau, Gundelfingen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 28 days.

(21) Appl. No.: 13/900,895

(22) Filed: May 23, 2013

(65) Prior Publication Data

US 2013/0314440 A1 Nov. 28, 2013

(30) Foreign Application Priority Data

May 23, 2012 (EP) .................................... 12169104

(51) Int. Cl.
*G06T 7/00* (2006.01)
*G06T 19/00* (2011.01)
*G06T 19/20* (2011.01)

(52) U.S. Cl.
CPC ............ *G06T 7/0024* (2013.01); *A61B 34/10* (2016.02); *G06T 7/004* (2013.01); *G06T 7/0014* (2013.01); *G06T 19/006* (2013.01); *G06T 19/20* (2013.01); *A61B 2034/102* (2016.02); *A61B 2090/376* (2016.02); *G06T 2207/10116* (2013.01); *G06T 2207/20092* (2013.01); *G06T 2207/20221* (2013.01); *G06T 2207/30008* (2013.01); *G06T 2219/2016* (2013.01)

(58) Field of Classification Search
None
See application file for complete search history.

(56) References Cited

U.S. PATENT DOCUMENTS

| 5,398,684 | A | 3/1995 | Hardy |
| 5,799,055 | A | 8/1998 | Peshkin et al. |
| 6,064,932 | A | 5/2000 | François |
| 6,198,794 | B1 | 3/2001 | Peshkin et al. |
| 6,701,174 | B1 | 3/2004 | Krause et al. |
| 6,711,432 | B1 | 3/2004 | Krause et al. |
| 2004/0111024 | A1* | 6/2004 | Zheng et al. ................. 600/426 |
| 2004/0240715 | A1 | 12/2004 | Wicker et al. |
| 2005/0251113 | A1 | 11/2005 | Kienzle |

(Continued)

FOREIGN PATENT DOCUMENTS

EP 2363083 A1 9/2011
WO 2004069040 A2 8/2004

(Continued)

OTHER PUBLICATIONS

Dahlen et a. "Computer-assistierte OP-Planung", Der Unfallchirurg, vol. 104, No. 6, Jun. 1, 2001, pp. 466-479, XP55036111.
Extended European Search Report for Application No. EP12169104 dated Sep. 3, 2012.

(Continued)

*Primary Examiner* — Jwalant Amin
(74) *Attorney, Agent, or Firm* — Lerner, David, Littenberg, Krumholz & Mentlik, LLP

(57) ABSTRACT

A method and device for assisting reduction for complex fractures includes the steps of receiving an x-ray image of a fractured bone having a plurality of bone fragments, identifying structural aspects of at least one of the bone fragments, adapting a virtual bone model to the imaged bone based on the identified structural aspects, and generating an overlay of the virtual bone model onto the x-ray image, with the virtual bone model aligned to the identified structural aspects. The device is adapted to perform the method.

18 Claims, 6 Drawing Sheets

(56) References Cited

U.S. PATENT DOCUMENTS

| | | |
|---|---|---|
| 2007/0270680 A1 | 11/2007 | Sheffer et al. |
| 2008/0075348 A1 | 3/2008 | Rappaport et al. |
| 2008/0175464 A1 | 7/2008 | Brett et al. |
| 2009/0017430 A1 | 1/2009 | Muller-Daniels et al. |
| 2009/0209851 A1 | 8/2009 | Blau |
| 2010/0063550 A1* | 3/2010 | Felix .............. A61B 17/7032 606/301 |
| 2010/0241129 A1 | 9/2010 | Markey et al. |
| 2011/0082367 A1 | 4/2011 | Regazzoni |
| 2011/0213379 A1 | 9/2011 | Blau et al. |
| 2012/0106819 A1* | 5/2012 | Fernandez Oca ............. 382/132 |
| 2013/0211386 A1 | 8/2013 | Blau et al. |
| 2013/0317512 A1 | 11/2013 | Buhren et al. |

FOREIGN PATENT DOCUMENTS

| | | |
|---|---|---|
| WO | 2010121147 A1 | 10/2010 |
| WO | 2010122145 A1 | 10/2010 |

OTHER PUBLICATIONS

Guoyan Zheng et al, "A hybrid CT-free navigation system for total hip arthroplasty", Computer Aided Surgery, vol. 7, No. 3, Jan. 1, 2002, pp. 129-145, XP55036140.

Schulz et al., "Evidence based development of a novel lateral fibula plate (VariAx Fibula) using a real CT bone data based optimization process during device development", The Open Orthopaedics Journal, 2012, 6, 1-7.

Zheng et al, "Reality-augmented virtual fluoroscopy for computer-assisted diaphyseal long bone fracture osteosynthesis: a novel technique and feasibility study results", Proceedings of the Institution of Mechanical Engineers.Journal of Engineering in Medicine. Part H, Mechanical Engineering Publications Ltd, London, GB, vol. 222, No. H1, Jan. 1, 2008, pp. 101-115, XP009162175.

International Search Report for Application No. PCT/EP2012/002207 dated Feb. 8, 2013.

International Search Report for Application No. PCT/EP2012/002206 dated Feb. 12, 2013.

* cited by examiner

VIRTUAL 3D OVERLAY AS REDUCTION AID FOR COMPLEX FRACTURES

CROSS-REFERENCE TO RELATED APPLICATION

The present application claims priority from European Patent Application No. 12169104.2 filed May 23, 2012, the disclosure of which is hereby incorporated herein by reference.

BACKGROUND OF THE INVENTION

The invention relates to the field of computer assisted surgery. In particular, the invention relates to a method and a device for assisting reduction of complex fractures. The method may be implemented as a computer program executable on a processing unit of the device, in accordance with the invention.

Usually, a bone fracture is treated without opening the tissue surrounding the fractured bone. In many cases it is possible to re-position the fragments of a bone by applying a force at the outer surface of the surrounding tissue, i.e. by pushing a portion of for example a leg or an arm. However, in case of complex fractures, an appropriate positioning of, in particular, smaller fragments is difficult. Furthermore, it may occur that a position and orientation of a first bone fragment relative to a second bone fragment, with further fragments in between, is not anatomically correct, the fragments may be shifted or inclined relative to each other

BRIEF SUMMARY OF THE INVENTION

It may be seen as an object to provide a method and a device for assisting a repositioning of fragments of a complex fracture. This is achieved by the subject-matter of each of the independent claims. Further embodiments are described in the respective dependent claims.

In general, a method for assisting reduction for complex fractures comprises the steps of receiving an x-ray image of a fractured bone having a plurality of bone fragments, identifying structural aspects of at least one of the bone fragments, adapting a virtual bone model to the imaged bone based on the identified structural aspects, and generating an overlay of the virtual bone model onto the x-ray image, with the virtual bone model aligned to the identified structural aspects.

Any bone of a human or animal body, in particular a long bone of the lower extremities, like the femur and the tibia, and of the upper extremities, like the humerus, may be subject to a method as described herein. That is, by means of an overlay of a corresponding bone model onto an image of any fractured bone assistance may be provided during the attempt to reposition fragments of the fractured bone, in particular in case of a complex fracture.

As used herein, the term "bone model" encompasses, for example, a 3D model of a bone. The bone model may be generated based on at least one 3D scan of at least one real bone of the same kind, for example a femur or humerus, and/or by forming an average from a plurality of 3D scans. Furthermore, the term "bone model" also encompasses a 2D model of a bone which may be generated by a projection of a 3D model or on the basis of one or more 2D projection images. An exemplary utilization of bone models is described in 'Evidence based development of a novel lateral fibula plate (VariAX Fibula) using a real CT bone data based optimization process during device development' of A. P. Schulz et al. (The Open Orthopaedics Journal, 2012, 6, 1-7), the content of which is incorporated herein by reference.

Accordingly, the method may further comprise the step of selecting a bone model from a group of bone models with different sizes and shapes, the selected bone model corresponding to the imaged bone. The group of bone models may be stored in a database. Further, the group of bone models may be a selection of previously generated images, each of another person, wherein the persons may differ in size, weight and age. The database may thus contain several models of each bone (e.g. tibia, femur, humerus) including bone models of different ages, genders and individual sizes. The software uses gray scale image data to determine at least one dimension from the x-ray (2D image) of one bone segment and searches the database for a bone model of a person of the same age, gender and size, for example, having an identical or at least a close approximation to the at least one dimension from the bone to be treated. When a match is determined a three dimensional model of the matched bone in the database is selected and utilized as a corresponding 3D bone model of the bone to be treated.

Furthermore, the method may further comprise the step of adapting a bone model so that the bone model corresponds to the imaged bone. Also here, the bone model may be stored in a database. In this case, the bone model may be generated by forming an average of a plurality of previously generated 2D or 3D images. To adapt the bone model to the imaged bone, substantially the size of the bone model may be increased or decreased so as to fit to the size of the bone as measured in the image.

As used herein, the term "structural aspect" refers to anything at a bone which can be identified, i.e. a point, a line, an arc, a center point, an axis, a cylinder surface, a ball surface, or the like. For example, a structural aspect of a femur may be the outer surface of the femur head, an axis defined by the neck between shaft and femur head, a longitudinal axis of the femur shaft, a most distal point on the bone surface, a line defined by the center points of the condyles, or a line defined by the most posterior points at the condyles. It will be understood that other bones provide other and/or comparable suitable structural aspects.

As used herein, the term "structural aspect" may also encompass any feature of an implant being already inserted into a bone or at least fixedly connected to a bone, said feature being suitable for determining a structural aspect as mentioned above.

According to an embodiment, at least one of the structural aspects is associated with a reference body, wherein the reference body may be adapted to be fixedly connected to the bone.

As used herein, each of the terms "fixedly connected", "fixedly coupled" and "fixedly attached" or the like, encompasses a direct as well as an indirect connection of an element to another element. For example, a reference body may be directly attached at an implant or may be indirectly coupled to an implant. On the other hand, a reference body which is integrated into an implant, i.e. which can be considered as fixedly connected to the implant, may be considered as being indirectly coupled to a bone, i.e. via the implant.

An implant which is adapted to be fixed at or in a bone may comprise elements which can be identified in an image of the bone or at least a section of the bone so that a location and/or an orientation of the implant may be determined based on the identified elements. For example, the elements may define points so that two elements may define a line or an axis, or the elements may define a contour so that a center axis may be determined.

According to an embodiment, the step of identifying structural aspects is performed automatically, for example based on grey scale image data.

According to another embodiment, a monitor is provided for visualizing the generated overlay of a bone model onto an imaged bone.

According to a further embodiment, the method does not include the step of introducing a reference body or an implant with reference elements into a human or animal body, and/or the step of bringing a reference body or an implant with reference elements in contact with a bone surface, and/or the step of attaching a reference body or an implant with reference elements at a bone fragment.

According to another embodiment, a device for assisting reduction of complex fractures is provided comprising a processing unit adapted to perform the above described steps.

It is noted, that the processing unit may be realized by only one processor performing all the steps of the method, or by a group or plurality of processors, for example a system processor for processing the image data, a separate processor specialized on a determination of structural aspects, and a further processor for controlling a monitor for visualizing the result.

According to an embodiment, the processing unit is further adapted to automatically perform the steps of identifying structural aspects of a bone fragment and/or adapting a virtual bone model to the imaged bone.

According to yet another embodiment, the device further comprises input means for manually identifying structural aspect of a bone fragment and/or for adapting a virtual bone model to the imaged bone.

It will be understood that also a combination of automatically performed steps and manually performed steps may also be suitable to achieve an appropriate result.

According to another embodiment, the device comprises storage means providing a database. It will be understood, that such storage means may also be provided in a network to which the device may be connected and information related to the bone model, i.e. different types of models and parameter thereof, may be received over that network.

According to an embodiment, the device further comprises an imaging unit for providing 2D projection image data of at least a section of the bone. The imaging unit may be capable of generating images from different directions. Accordingly, the imaging unit of the device may be adapted to also provide 3D image data of at least a section of the bone.

According to yet another embodiment, the processing unit of the device is further adapted for identifying a reference body in a projection image and adapted for determining a 3D position and orientation of the reference body.

According to a further embodiment, the device further comprises a reference body including an arrangement of elements which allows a reconstruction of a 3D orientation of the reference body based on a single 2D projection image.

The device may further comprise input means for manually identifying structural aspects of a bone in an image. Such input device may be for example a computer keyboard, a computer mouse, a touch screen or a voice control device.

According to a further embodiment, a computer software is provided including sets of instructions which when executed on an appropriate device, like for example a device with the above described features, causes the device to perform at least the steps of the method as described above.

A corresponding computer program is preferably loaded into a work memory of a data processor. The data processor or processing unit is thus equipped to carry out one of the described methods. Further, the invention relates to a computer-readable medium such as a CD-ROM at which the computer program may be stored. However, the computer program may also be presented over a network like the World Wide Web and can be downloaded into the working memory of the data processor from such a network.

It has to be noted that embodiments are described with reference to different subject-matters. In particular, some embodiments are described with reference to method type claims (computer program) whereas other embodiments are described with reference to apparatus type claims (device). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages can also be derived from the examples of the embodiments to be described hereinafter and are explained with reference to examples of embodiments also shown in the figures, but to which the invention is not limited

Figure 1:
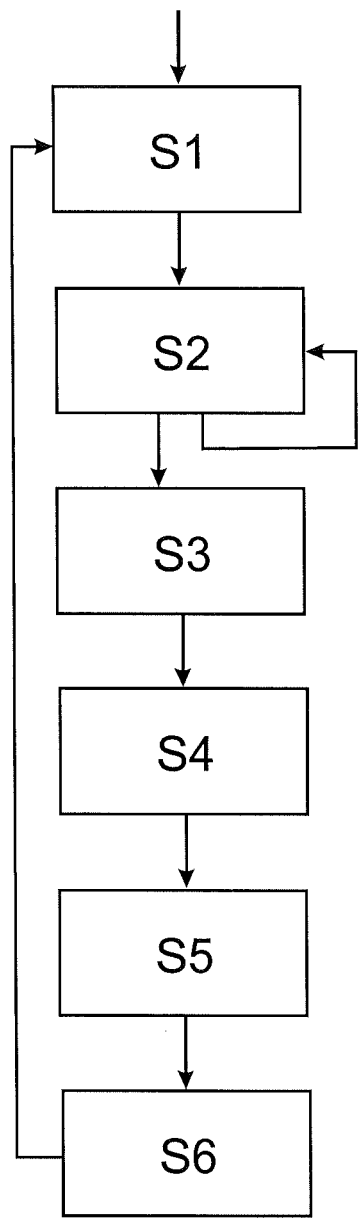
FIG. 1 shows a flow chart of steps perfumed in accordance with an embodiment.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

The flow-chart in FIG. 1 illustrates the principle of the steps performed in accordance with one embodiment of a method. It will be understood that the steps described, are major steps, wherein these major steps might be differentiated or divided into several sub-steps. Furthermore, there might be also sub-steps between these major steps.

In accordance with one method, in step S1, an X-ray image of at least a portion of a bone is received, wherein the X-ray image includes a plurality of bone fragments.

As used herein, the term "receiving an image" basically refers to the fact that at least one image is necessary to perform the subsequent steps. That is, the term "receiving an image" may encompass also a loading of an image from a data memory into a processing unit. There is no need to generate a new image to receive an image. Accordingly, the image received in step S1, may be any image suitable to identify for example a longitudinal axis of a bone or another feature of the bone, i.e. a 3D image or a 2D image of at least the respective section of the bone, wherein the 2D image may additionally show a reference body.

In step S2, at least one structural aspect at the imaged bone is identified. That is, at one of the bone fragments shown in the X-ray image, a structural aspect is identified. For example, the outer surface of a bone joint element at one of the ends of a bone or a longitudinal axis of a bone shaft may be identified (manually or automatically).

It will be understood, that step S2 may be performed several times, in case it is necessary to identify more than one structural aspect at one or more than one bone fragment. For example, a longitudinal axis at a first bone fragment and a longitudinal axis at a second bone fragment may be identified. This repetition of step S2 is indicated by the arrow loop at step S2 in FIG. 1.

In step S3, which may be an optional step, a reference body is identified, wherein the reference body may be associated to one of the bone fragments. For example, a reference body may be formed by a plurality of radiopaque elements which are provided with a predetermined 3D position relative to each other. Such elements may be arranged at or in an implant, wherein the implant may be adapted to be fixedly connected to one of the bone fragments.

In step S4, data of a virtual bone model are received and the virtual bone model is adapted to the imaged bone, if necessary.

In step S5, the virtual bone model is registered with the imaged bone so that corresponding features of the imaged bone and the bone model can be shown as an overlay.

Sub-steps of S5 may be that a first feature of the bone model is registered with the corresponding feature of a first fragment of the imaged bone, and that subsequently a second feature of the bone model is registered as close as possible with the corresponding feature of a second fragment of the bone. It will be understood that, in case of a complex fracture, the fragments of a fractured bone may be positioned and orientated relative to each other in an un-natural way, so that it can be expected that the bone model has to be visualized over the imaged bone with a deviation with respect to the identified structural aspects.

In step S6, the overlay of the imaged bone and the bone model is shown on a monitor. As indicated by the arrow from step S6 back to step S1, the method may be repeated, for example based on an X-ray image generated from another direction.

Figure 2:
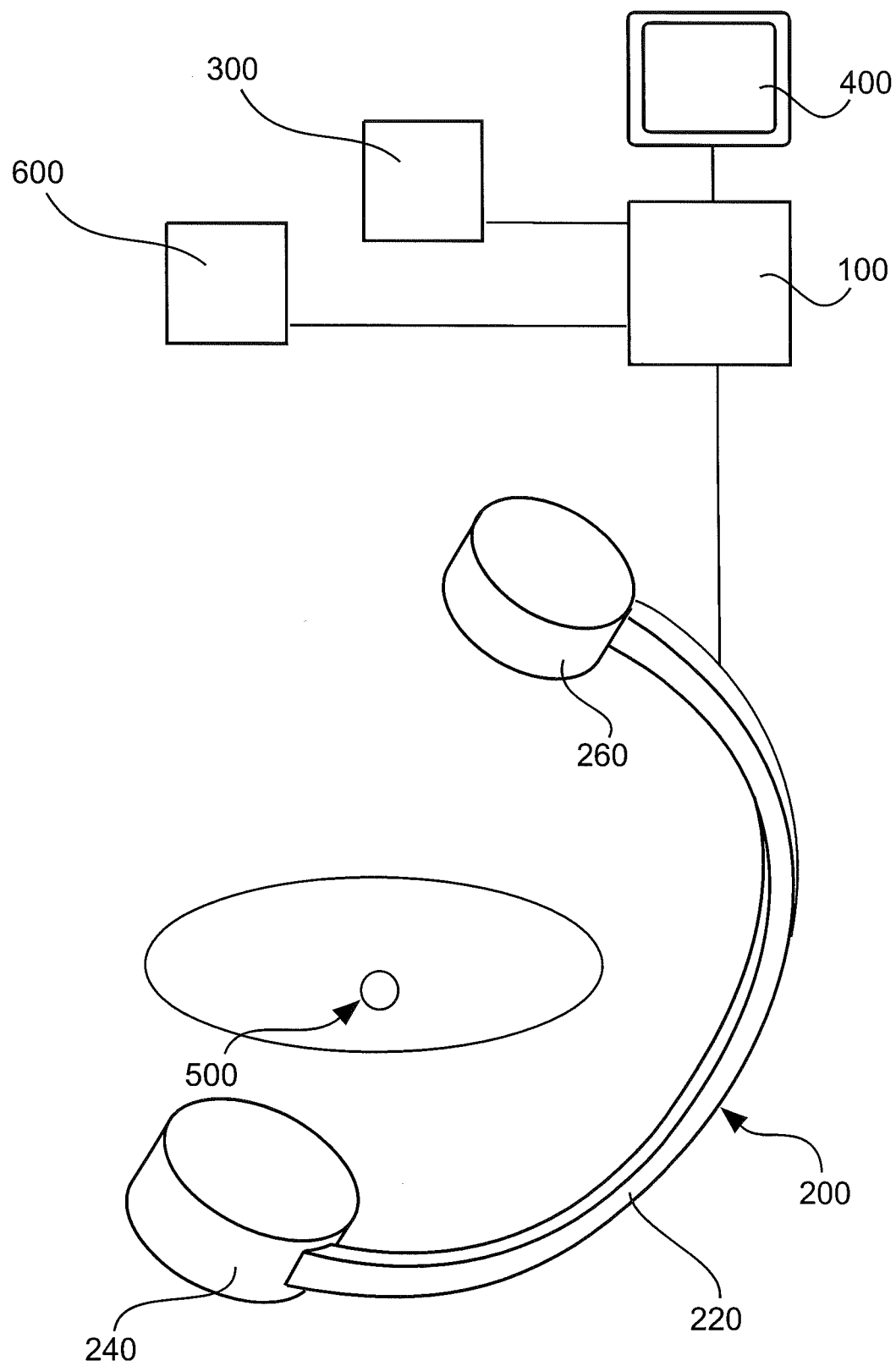
FIG. 2 shows a schematical illustration of a system according to an embodiment.

FIG. 2 shows an exemplary embodiment of a device. Substantially, necessary for performing the steps according to the method, a processing unit 100 together with a monitor 400 is part of the device.

An exemplary imaging device 200 includes an X-ray source 240, and an X-ray detector 260, wherein these two devices are mounted on a C-arm 220. It will be understood that the device may also comprise a non-invasive imaging modality like a computer tomography device, a magnetic resonance device, or an ultrasound device as imaging device instead of or additional to the shown C-arm based X-ray device.

Furthermore, the system in FIG. 2 includes an input device 300, by means of which for example a manual determination of a bone feature may be performed. Also shown is a connection to a database 600, located for example in a network.

Finally, there is shown a region of interest 500. Within said region, for example a bone of a patient may be located which is subject to the method according to one embodiment.

FIGS. 3 to 6 show schematically illustrations of exemplary images which may be achieved by the method and/or the device. The figures show the outlines of anatomical structures, in particular of the hip bone and the upper leg bone, i.e. a femur. In the shown example, the femur is fractured at the upper end of the femur shaft and at the neck of the femur. The femur comprises four fragments, namely a fragment 10 including the femur head, a fragment 13 including the femur shaft, and two fragments 11 and 12 formed by intermediate parts of the femur. A fracture F1 extends through the femur neck between fragments 10 and 11, a fracture F2 extends between fragments 11 and 12, and a fracture F3 extends through the femur shaft between fragments 12 and 13.

Figure 3:
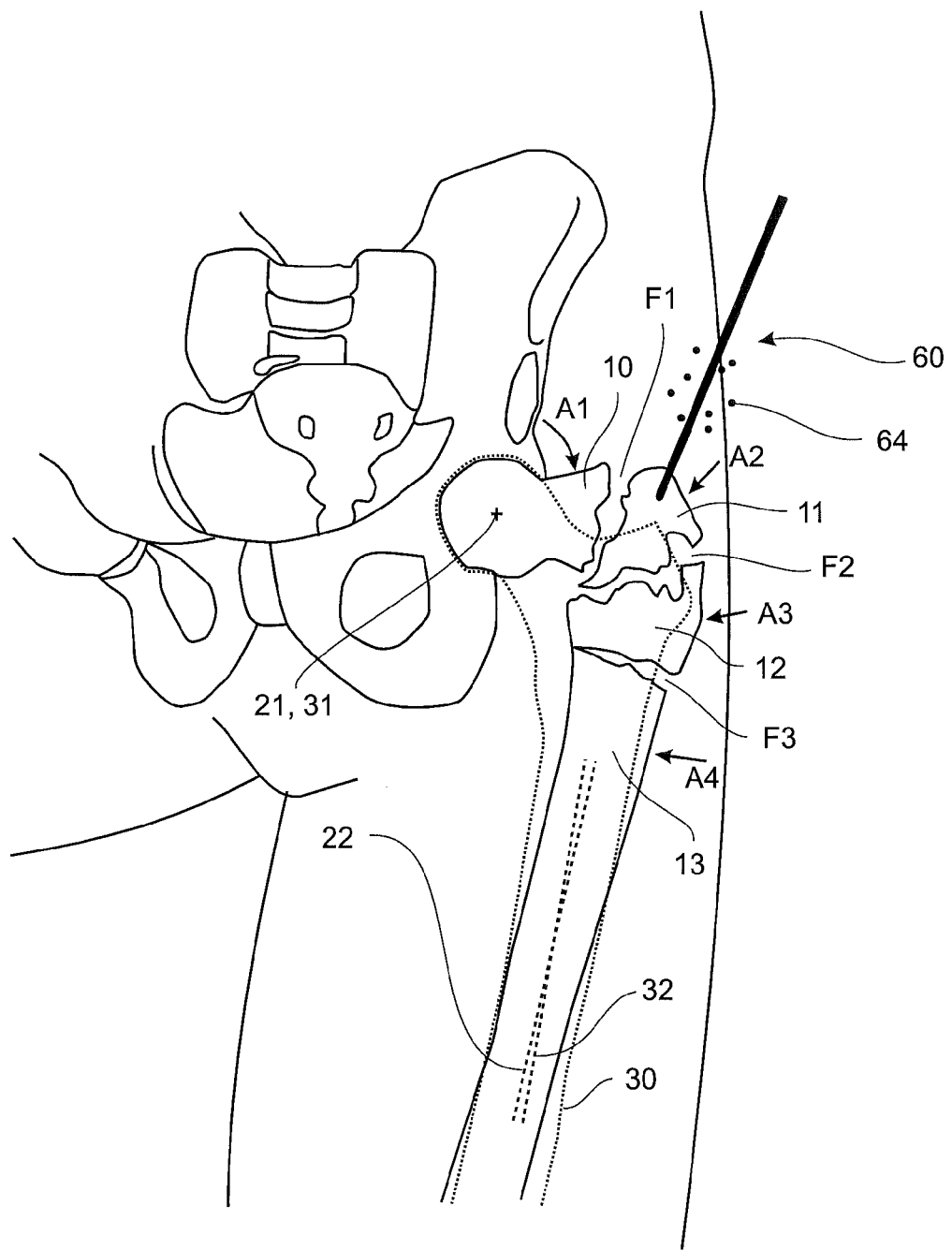
FIG. 3 shows an exemplary illustration of a fractured femur in an anterior to posterior direction together with a bone model as an overlay.

FIG. 3 is an image generated in an anterior to posterior direction, i.e. from above (assuming that the patient is lying on his/her back). FIG. 3 illustrates a situation before a repositioning of any of the bone fragments.

As can be seen, a bone model 30 of the femur is introduced into the image, the bone model being illustrated in dotted lines. It will be understood that a bone model may also be shown coloured and/or as a three-dimensional visualization. Furthermore, the bone model may be illustrated at least to some extent transparent.

In FIG. 3, the bone model 30 is positioned so that the centre point 31 of the femur head of the bone model 30 is at the position of the centre point 21 of the imaged femur head. It is noted that this point is an appropriate anchor point for the bone model, as long as the femur head is further on accommodated in the joint structure of the hip bone (acetabulum). The centre point 21, 31 of the femur head of the imaged bone as well as of the bone model may be determined based on the outer contour line of the femur head forming a circle or ball around the centre point.

As a further structural aspect, the longitudinal axis 22 of the bone fragment 13 with the shaft of the femur is determined. This structural aspect is used as a second aspect to register the bone model more or less over the image bone fragments. Assuming that the fragment 13 is dislocated due to the complex fracture, the longitudinal axis 32 of the bone model 30 may deviate from the longitudinal axis 22 of the bone fragment 13, i.e. the longitudinal axis 32 of the bone model may be inclined relative to the axis 22 of the bone fragment 13, as shown in FIG. 3.

Based on such an image, a physician may easily see in which direction and how far each of the fragments should be pushed to be in an anatomically correct position. Here, fragment 10 should be pivoted around the centre point 21 (as indicated by arrow A1), fragment 11 should be pushed in a direction to medial and distal (as indicated by arrow A2), fragment 12 should be pushed similar to fragment 11 (as indicated by arrow A3), and fragment 13 should be pushed more or less in a medial direction (as indicated by arrow A4). It is noted that the processing unit may further be adapted to automatically indicate in an image the directions and distances for the repositioning of the respective bone fragments to fit to the corresponding portions of the bone model.

Furthermore, a reference body 60 is shown in FIG. 3, wherein the reference body is fixedly connected to bone fragment 11. The reference body 60 comprises reference elements 64, wherein the position and, in particular, the 3D orientation of the reference body 60 can be determined based on a single 2D projection image, due to the characteristic distribution of the reference elements 64. By means of the reference body 60, a physician may have the additional possibility to hold or move the fragment 11 to which the reference body is attached. A further advantage of such a reference body is that the portion of the human body including the complex fracture may be determined automatically.

After repositioning the fragments at least in a horizontal plane (further on assuming that the image is generated in a vertical direction), an image may be generated for controlling the results of the repositioning. This image may be as shown in FIG. 4.

Figure 4:
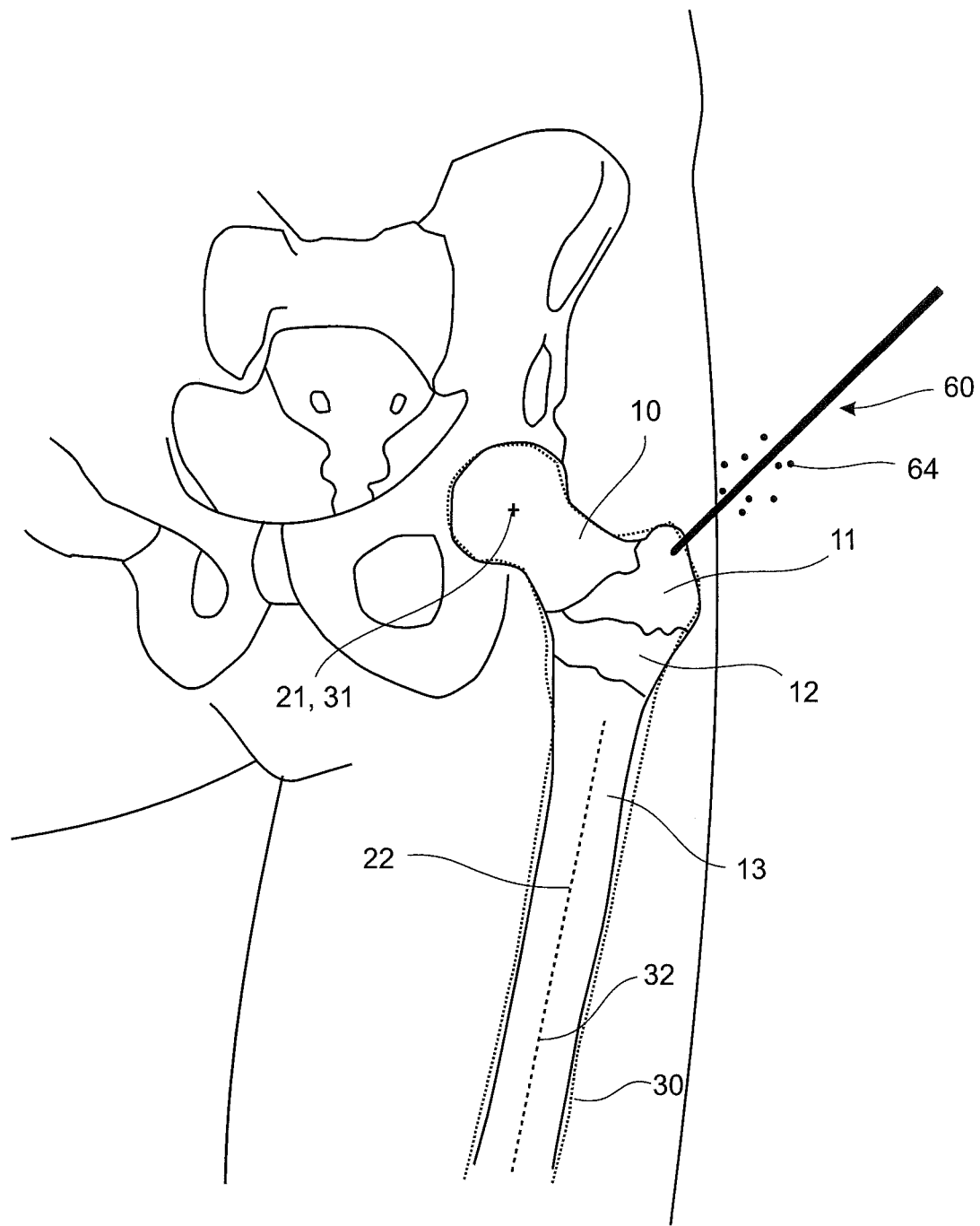
FIG. 4 shows the fractured femur of FIG. 3 after a re-positioning of the bone fragments

As can be seen in FIG. 4, the bone fragments 10, 11, 12, 13 are positioned relative to each other so that the femur fits into the contour of the bone model 30 which is shown as an overlay onto the imaged bone. In this situation, not only the first structural aspect (center point of the femur head) of the imaged bone and the bone model are congruent but also the second structural aspect (longitudinal axis of the shaft) of the imaged bone and the bone model are congruent with each other.

However, the images of FIGS. 3 and 4 do not take into account a vertical displacement of any of the fragment relative to the other fragments, i.e. as to whether the one or the other fragment is shifted in an anterior to posterior direction.

To improve the results of the computer assisted method, a further image generated from a different direction should be provided. Although any other direction may be possible, it would be preferred to generate the further image from a lateral to medial direction, i.e. from the side of the patient, especially in a case in which the first images have been generated in an anterior to posterior direction.

Figure 5:
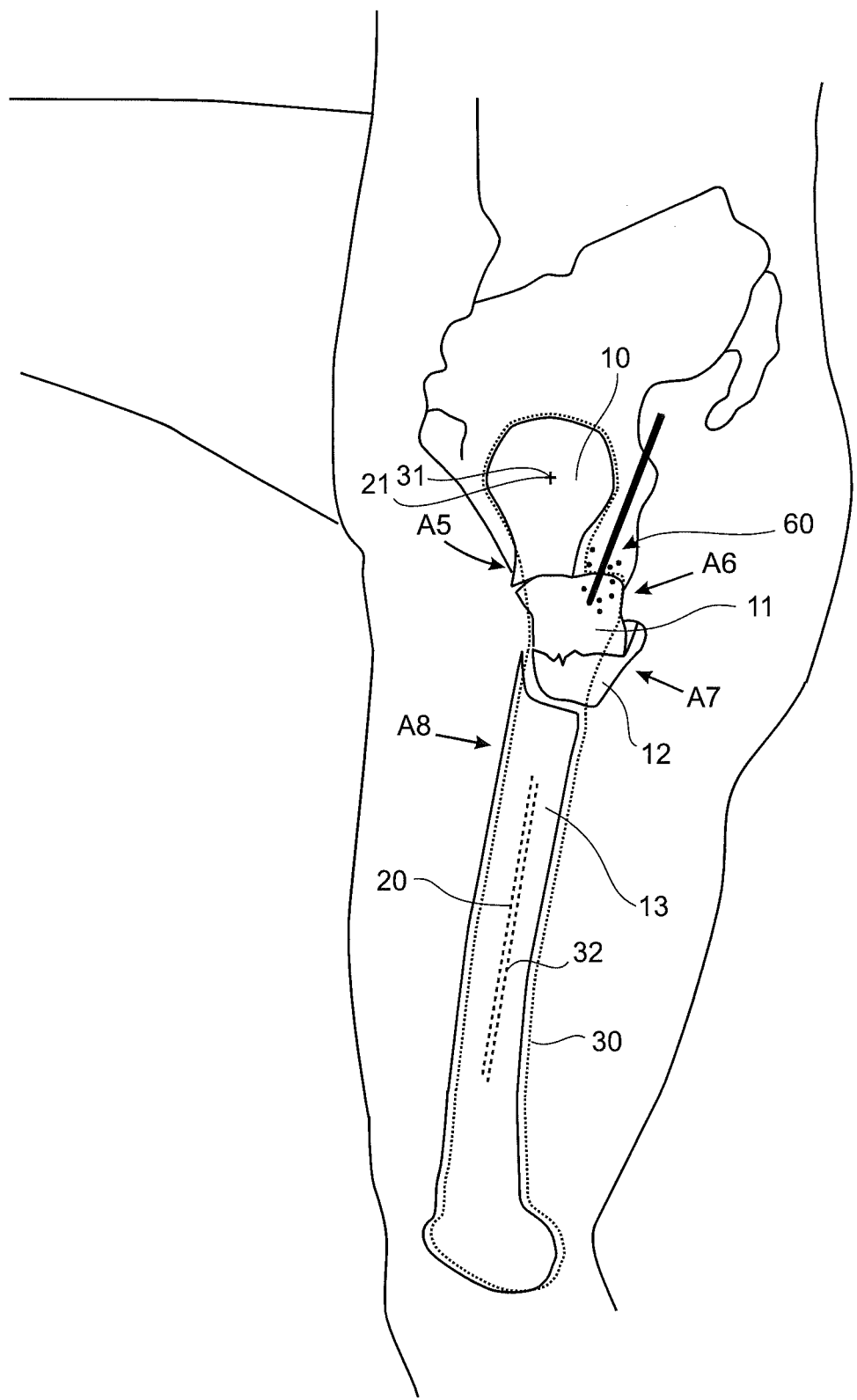
FIG. 5 shows an illustration of the fractured femur in a lateral to medial direction together with a bone model as an overlay.

FIG. 5 shows an image of an example in a situation in which the fragments are already repositioned in a horizontal direction, but are additionally dislocated in a vertical direction. Also here, a bone model 30 is introduced as an overlay onto the imaged bone, the bone model been positioned so that the centre point 31 of the femur head of the bone model is at the position of the corresponding centre point 21 of the imaged bone, and so that the longitudinal axis 32 of the shaft of the bone model is aligned, but parallel shifted to the longitudinal axis 22 of the shaft of the imaged bone.

As illustrated in FIG. 5, the fragment 10 including the femur head is slightly pivoted away from the anatomical orientation, the fragments 11 and 12 are shifted in a posterior direction, i.e. backwardly, the fragment 13 is displaced in an anterior direction, i.e. forwardly. Accordingly, the fragments 10 and 13 should be pushed in a posterior direction (as indicated by arrows A5 and A8) and the fragments 11 and 12 should be pushed in an opposite direction, i.e. in an anterior direction (as indicated by arrows A6 and A7).

Figure 6:
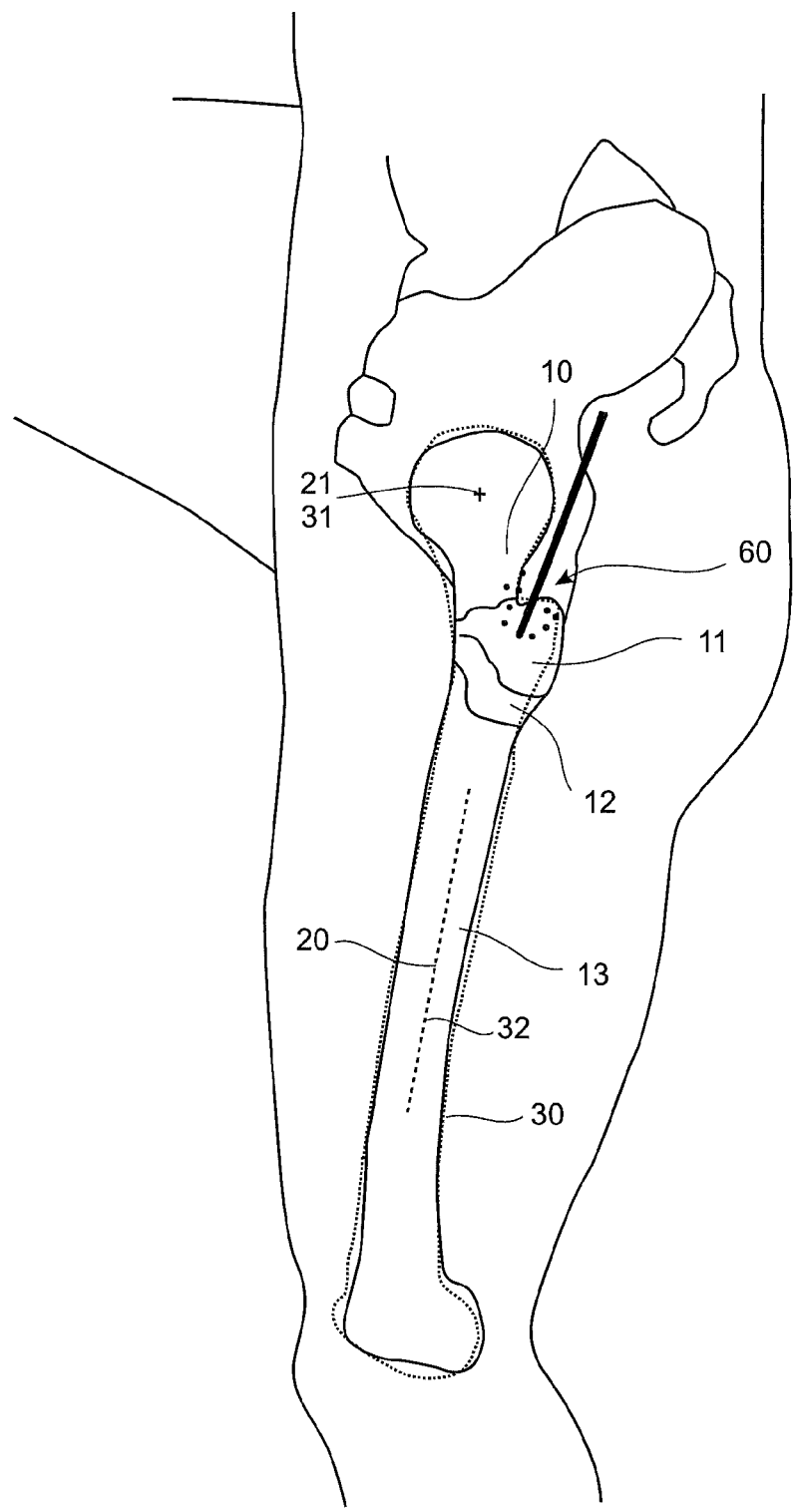
FIG. 6 shows the fractured femur of FIG. 5 after a re-positioning of the bone fragments.

In FIG. 6, a situation is shown in which the fragments 10, 11, 12, 13 are repositioned so as to be located at or in the contour of the bone model 30 which is visualized as an overlay in dotted lines.

As in the previous figures, reference body 60 is further depicted in FIGS. 5 and 6.

It is noted that the steps S1 to S6 may be repeated from a further direction or again from the first direction to control the results of the repositioning.

While embodiments has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures cannot be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for assisting reduction for complex fractures, the method comprising:
    receiving an x-ray image of a fractured bone having a plurality of bone fragments, a reference body connected to a bone fragment of the plurality of bone fragments of the fractured bone, the reference body having a plurality of radiopaque elements provided in a predetermined three-dimensional pattern within the reference body, the radiopaque elements spaced from the bone fragment;
    utilizing the plurality of radiopaque elements of the reference body to register the location of the bone fragments;
    identifying on the image at least one structural aspect of at least one of the bone fragments, the structural aspect selected from the group consisting of a point, a line, an arc, a centerpoint, an axis, a cylindrical surface, and a spherical surface;
    adapting a virtual bone model selected from a database of non-fractured virtual bone models to the imaged fractured bone based on the at least one identified structural aspect;
    using a computer to generate an overlay of the virtual bone model onto the x-ray image, with the virtual bone model aligned to the at least one identified structural aspect of the at least one bone fragment using the reference body; and
    repositioning the plurality of bone fragments so that the bone fragments fit into the contour of the selected non-fractured vertical bone model.

2. The method of claim 1, wherein the identification of the at least one structural aspects is performed automatically by the computer.

3. The method of claim 1, wherein the at least one structural aspect is a longitudinal axis of the imaged bone.

4. The method of claim 1, wherein the at least one structural aspect is a structural aspect of a joint portion of an imaged fractured bone.

5. The method of claim 1, wherein the at least one structural aspect is associated with the reference body.

6. The method of claim 1, further comprising the step of visualizing the generated computer overlay on a computer monitor.

7. The method of claim 1, further comprising an input for the computer for manually identifying the structural aspect of a bone fragment and for adapting the virtual bone model to the imaged bone.

8. The method of claim 7, further comprising a monitor for visualizing the overlay of the virtual bone model onto the x-ray image.

9. The method of claim 1, wherein the computer has processing unit adapted to automatically perform the steps of identifying structural aspects of the bone fragment and adapting the virtual bone model to the imaged bone.

10. The method of claim 1, further comprising a reference body adapted to be visible in the x-ray image of the fractured bone so as to identify the at lease one structural aspect of the at least one bone fragment to which structural aspect the reference body is associated.

11. The method as set forth in claim 1 wherein the reference body is coupled directly to the fractured bone.

12. A method for assisting reduction for complex femoral fractures, the method comprising the steps of:
receiving digital x-ray image of a fractured femur having a plurality of bone fragments, the image including a reference body connected to one of the plurality of bone fragments of the fractured femur, the reference body having a plurality of radiopaque elements provided in a predetermined three-dimensional pattern within the reference body, the radiopaque elements spaced from the bone fragment;
utilizing the plurality of radiopaque elements of the reference body in the digital x-ray image to register the location of the bone fragments;
identifying a longitudinal axis and a femoral head center of the fractured femur and at least one structural aspect of at least one of the bone fragments;
adapting a virtual femur model selected from a group of actual non-fractured femur models stored in a database to the imaged fractured femur based on the identified longitudinal axis and the structural aspects of the bone fragments,
using a computer to generate an overlay of the virtual femur model onto the x-ray image, with a longitudinal axis and a femoral head center of the virtual femur model aligned to the longitudinal axis, head center and the identified structural aspects of the fractured femur using the reference body; and
repositioning the bone fragments to an anatomically correct position by fitting the bone fragments within the contour of the overlaid virtual bone model.

13. The method of claim 12, wherein the identification of structural aspects is performed by the computer automatically.

14. The method of claim 12, wherein at least one of the structural aspects is an aspect of a joint of the imaged bone.

15. The method of claim 12, wherein the at least one of the structural aspect is associated with the reference body.

16. The method of claim 12, further comprising the step of visualizing the generated overlay on a computer monitor.

17. The method as set forth in claim 12 further comprising fixedly connecting a reference body to a bone fragment, the reference body comprising radiopaque elements wherein the three dimensional orientation of the reference body can be determined from a two dimensional image.

18. The method as set forth in claim 11 wherein the reference body is coupled to one of the bone fragments of the fractured bone.

* * * * *